United States Patent
Piot et al.

[11] Patent Number: 5,866,149
[45] Date of Patent: Feb. 2, 1999

[54] COMPOSITION FOR MAKING UP THE EYELASHES AND THE EYEBROWS STABILIZED OXYETHYLENATED DERIVATIVES

[75] Inventors: Bertrand Piot, La Garenne-Colombes; Sylvie Sirugue, Bourg-la-Reine; Jeanne Patraud; Marie José Martin, both of Paris, all of France

[73] Assignee: L'Oreal, Paris, France

[21] Appl. No.: 917,691

[22] Filed: Aug. 26, 1997

Related U.S. Application Data

[63] Continuation of Ser. No. 492,073, filed as PCT/FR94/01444, Dec. 9, 1994, published as WO95/15741, Jun. 15, 1995, abandoned.

[30] Foreign Application Priority Data

Dec. 10, 1993 [FR] France ................................ 93 14882

[51] Int. Cl.$^6$ .................................................. A61K 7/40
[52] U.S. Cl. ........................... 424/401; 424/69; 424/70.7
[58] Field of Search .............................. 424/69, 401, 70.7

[56] References Cited

U.S. PATENT DOCUMENTS

Re. 29,871  12/1978  Papantoniou .............................. 424/64
4,608,392    8/1986  Jacquet et al. ........................... 514/844

FOREIGN PATENT DOCUMENTS 0 024 031  2/1981   European Pat. Off. .
0 243 145  10/1987  European Pat. Off. .
0 394 078  10/1990  European Pat. Off. .
0 466 094  9/1991   European Pat. Off. .
0 557 196  8/1993   European Pat. Off. .
2 666 105  2/1992   France .
2 167 301  5/1986   United Kingdom .

OTHER PUBLICATIONS

Abstract, JP A 58 180 410, 21 Oct. 1983.

*Primary Examiner*—Thurman K. Page
*Assistant Examiner*—D. Faulkner
*Attorney, Agent, or Firm*—Jacobson, Price, Holman & Stern, PLLC

[57] ABSTRACT

The present invention relates to a composition for making up the eyelashes and the eyebrows, consisting of a fatty phase based on wax(es) of melting point between 50° and 110° C. and of an aqueous phase based on water-soluble film-forming polymer(s) in solution, containing as emulsifying agent and agent for inhibiting the growth of microorganisms, a mixture comprising at least one oxyethylenated glyceryl ($C_{10}$–$C_{20}$) acylate and at least a second oxyethylenated glyceryl ($C_{10}$–$C_{20}$) acylate or a non-oxyethylenated glyceryl acylate, which are chosen such that the final HLB, in the Griffin sense, of the said mixture is between 6 and 15, and containing from 0 to 14% by weight of wax(es) I having a needle penetration at 25%, according to the Reinhold standard, between 1 and 7.5 and from 2 to 40% by weight of wax(es) II having a needle penetration at 25%, according to the Reinhold standard, between 7.5 and 217; the wax(es) I/wax(es) II weight ratio being less than 2.

17 Claims, No Drawings

COMPOSITION FOR MAKING UP THE EYELASHES AND THE EYEBROWS STABILIZED OXYETHYLENATED DERIVATIVES

This application is a continuation of application Ser. No. 08/492,073, filed Aug, 4, 1995, now abandoned, which is a 371 of PCT/FR94/01444, filed Dec. 9, 1994, published as WO95/15741 Jun. 15, 1995.

The present invention relates to compositions for making up the eyelashes and the eyebrows, consisting of a wax-based fatty phase dispersed in an aqueous phase containing water-soluble film-forming polymer(s), the dispersion being stabilized with a mixture of oxyethylenated glyceryl acylates or a mixture of oxyethylenated and non-oxyethylenated glyceryl acylates.

Generally, mascaras are wax-in-water emulsions whose physical stability is provided by the presence of surface-active agents and whose bacteriological stability is provided by the presence of preserving agents in sufficient amount.

However, these make-up compositions are poorly tolerated by individuals having very sensitive eyes. The presence, in these products, of certain irritant preserving agents or surfactants cause discomfort to these individuals.

Mascaras should also have good cosmetic properties. In particular, made-up eyelashes should be flexible, thereby making the make-up comfortable for the user.

The aim of the present invention is thus to produce stable mascaras which retain the flexibility of made-up eyelashes and which may be perfectly tolerated by sensitive eyes.

The Applicant has found, surprisingly, that certain specific mixtures of glyceryl acylates made it possible physically and bacteriologically to stabilize make-up compositions consisting of a wax-based fatty phase and of an aqueous phase based on film-forming polymer(s) in solution. Moreover, the Applicant has observed that these mixtures of emulsifying nonionic surfactants made it possible to obtain make-up products whose tolerance properties are satisfactory even for the most sensitive eyes.

The bactericidal properties of these specific mixtures of glyceryl acylates make it possible to avoid the use of preserving agents in the mascaras or to reduce substantially their content of preserving agents and thereby to improve their tolerance with respect to the most sensitive eyes.

The Applicant has also discovered that by using these specific mixtures of glyceryl acylates in make-up compositions containing a specific wax formulation, mascaras having both good bactericidal properties and good flexibility properties were obtained.

The subject of the present invention is thus a composition for making up the eyelashes and the eyebrows which contains a fatty phase based on a specific wax formulation defined below, and, as emulsifying and bactericidal agents, a mixture of glyceryl acylates defined below.

Another subject of the invention is a process for the preparation of these make-up compositions.

Other subjects will emerge on reading the description and the examples which follow.

The flexible compositions for making up the eyelashes and the eyebrows, according to the invention, consist of a phase based on wax(es) having a melting point between 50° and 110° C. and an aqueous phase based on water-soluble film-forming polymer(s) in solution. They are characterized in that they contain:

(a) from 0 to 14% by weight of wax(es) I having a needle penetration index at 25° C., measured according to the Reinhold standard, between 1 and 7.5 and from 2 to 40% by weight of wax(es) II having a penetration index, measured at 25° C. according to the same standard, between 7.5 and 217; the wax(es) of the type I/wax(es) of the type II weight ratio being less than 2; and (b) as emulsifying agent and agent for inhibiting the growth of microorganisms, a mixture comprising at least one oxyethylenated glyceryl ($C_{10}$–$C_{20}$) acylate and at least a second oxyethylenated glyceryl ($C_{10}$–$C_{20}$) acylate or a non-oxyethylenated glyceryl ($C_{10}$–$C_{20}$) acylate, chosen such that the final hydrophilic-lipophilic balance or HLB, in the Griffin sense, of the said mixture is between 6 and 15. The HLB value according to Griffin is defined in J. Soc. Cosm. Chem. 1954 (volume 5), pages 249–256.

The final HLB of the emulsifying mixture is preferably between 9 and 13.5.

The final HLB of a mixture consisting of two glyceryl acylates A and B according to the invention is determined by calculation from the following ratio:

$$\text{Final } HLB = \frac{XA \times HLBA + YB \times HLBB}{XA + YB}$$

where

XA represents the percentage by weight of the component A in the final composition;

YB represents the percentage by weight of the component B;

HLBA and HLBB are the respective HLB values of the components A and B.

The oxyethylenated and non-oxyethylenated glyceryl acylates used according to the invention are mono- or polyesters having a degree of saturation from 0 to 3, preferably 0. The number of moles of ethylene oxide ranges from 0 to 100, preferably from 0 to 30, and more preferably from 15 to 30.

Among the non-oxyethylenated glyceryl acylates used according to the invention, there may, for example, be mentioned:
  glyceryl stearate, such as the product sold under the name TEGIN M by the company Goldschmidt;
  glyceryl laurate, such as the product sold under the name IMWITOR 312 by the company Hüls.

Among the oxyethylenated glyceryl acylates used according to the invention, there may be mentioned:
  glyceryl stearate polyethoxylated with 30 mol of ethylene oxide, such as the product TAGAT S sold by the company Goldschmidt;
  glyceryl oleate polyethoxylated with 30 mol of ethylene oxide, such as the product TAGAT O sold by the company Goldschmidt;
  glyceryl cocoate polyethoxylated with 30 mol of ethylene oxide, such as the product VARIONIC LI 13 sold by the company Sherex;
  glyceryl isostearate polyethoxylated with 30 mol of ethylene oxide, such as the product TAGAT L sold by the company Goldschmidt;
  glyceryl laurate polyethoxylated with 30 mol of ethylene oxide, such as the product TAGAT I from the company Goldschmidt;
  glyceryl trioleate polyethoxylated with 25 mol of ethylene oxide, such as the product TAGAT TO from the company Goldschmidt.

The preferred emulsifying mixtures according to the invention consist of an oxyethylenated glyceryl ($C_{10}$–$C_{20}$)

acylate such as those mentioned above, in particular oxyethylenated glyceryl stearate whose ethylene oxide number is between 15 and 30, and glyceryl stearate.

The emulsifying mixture according to the present invention is present in the compositions of the invention in a proportion between 0.5 and 15% by weight, preferably between 3 and 13% by weight, relative to the total weight of the composition.

The waxes uses in accordance with the present invention have a melting point between 50° and 110° C. and a penetration index at 25° C., measured according to the Reinhold standard, between 1 and 7.5 (class I) or between 7.5 and 217 (class II).

The principle of the needle penetration measurement according to A. Warth Reinhold is described in "The chemistry and technology of Waxes" by Albin Warth Reinhold, publishing corporation New York, 1947. It consists in measuring the depth, expressed in millimeters, to which a standardized needle (weighing 100 g) placed on the wax penetrates in 5 seconds.

The waxes used in accordance with the invention are chosen from animal waxes, plant waxes, mineral waxes, synthetic waxes and various fractions of natural waxes; all these waxes have the two characteristics mentioned above.

The waxes of class I are chosen in particular from candelilla wax, carnauba wax, ouricury wax, sugar cane wax and certain polyethylene waxes of molecular weight such that they fulfil the criteria of the waxes I.

They are present in proportions between 0 and 14% by weight relative to the total weight of the composition.

The waxes of class II, according to the invention, are chosen in particular from beeswax, lanolin waxes, paraffin waxes, cerasin waxes, microcrystalline waxes, ozokerites, spermacetis, certain polyethylene waxes of molecular weight such that they fulfil the criteria of the waxes II, and hydrogenated plant oils.

Among the hydrogenated plant oils, there may be mentioned hydrogenated jojoba waxes and hydrogenated oils which are obtained by catalytic hydrogenation of fatty substances composed of linear or non-linear $C_8$–$C_{32}$ fatty chain and which have the qualities corresponding to the definition of waxes. There may in particular be mentioned hydrogenated sunflower oil, hydrogenated castor oil, hydrogenated coconut oil and hydrogenated lanolin.

They are present in the composition of the invention in proportions between 2 and 40% by weight, and preferably between 2 and 30% by weight, relative to the total weight of the composition.

The wax(es) I/wax(es) II weight ratio is preferably less than 1.25.

The make-up compositions according to the invention are preferably in the form of a wax-in-water emulsion in which the size of the dispersed wax particles is greater than 1 μm. This specific form of emulsion makes it possible to reduce further the content of preserving agents compared with a microemulsion (microdispersion of wax particles which are smaller than 1 μm in size) for an equivalent bactericidal activity.

In accordance with another characteristic of the compositions according to the invention, the weight ratio of the emulsifying mixture used to the amount of wax used is between 0.10 and 0.6, preferably between 0.3 and 0.5.

The compositions according to the present invention may also contain fillers. The fillers are either colored (pigments) or noncolored.

The pigments which may be used in accordance with the invention are chosen from inorganic pigments, organic pigments and pearlescent pigments.

As examples of inorganic pigments, there may be mentioned titanium dioxide (rutile or anatase) optionally surface treated and listed in the Color Index under the reference (CI 77 891), black, yellow and red iron oxides (CI 77 499–CI 77 492–CI 77 491) and manganese violet (CI 77 742), ultramarine blue (CI 77 007), chromium oxide (CI 77 288), chromium hydrate (CI 77 289) and ferric blue (CI 77 510).

The organic pigments are chosen, in particular, from carbon black, pigments D and C red No. 19 (CI 45 170), D and C red No. 9 (CI 15 585), D and C red No. 21 (CI 45 380), D and C orange No. 4 (CI 15 510), D and C orange No. 5 (CI 45 370), D and C red No. 28 (CI 45 410), D and C red No. 13 (CI 15 630), D and C red No. 57 (CI 15 850), D and C yellow No. 23 (CI 19 140), D and C red No. 36 (CI 12 085), D and C acid red No. 95 (CI 45 425), D and C yellow No. 6 (CI 15 985), D and C red No. 30 (CI 73 360), D and C red No. 3 (CI 45 430), and lakes based on cochineal carmine (CI 75 470).

The pearlescent pigments may be chosen from white pearlescent pigments such as mica coated with titanium oxide, bismuth oxychloride, colored pearlescent pigments such as titanium mica with iron oxides, titanium mica with ferric blue, with chromium oxide, etc., titanium mica with an organic pigment of the abovementioned type, and those based on bismuth oxychloride.

When they are used, the pigments are present in proportions from 0.5 to 10% by weight relative to the total weight of the composition, depending on the coloration and the intensity of the coloration which it is desired to obtain.

The noncolored fillers are chosen in particular from:
  talc, which is a hydrated magnesium silicate in the form of particles generally smaller than 40 μm in size;
  micas, which are aluminosilicates of varied composition and are in the form of flakes 2 to 200 μm, preferably 5 to 70 μm in size and 0.1 to 5 μm, preferably 0.2 to 3 μm in thickness. The micas may be of natural origin (for example muscovite, margarite, roscoelite, lipidolhite and biotite) or of synthetic origin;
  starch, in particular rice starch;
  kaolin, which is a hydrated aluminum silicate and is in the form of particles of isotropic form generally smaller than 30 μm in size;
  zinc oxide and titanium oxide, which are generally used in the form of particles not exceeding a few micrometers in size (or even smaller than 1 μm in the case of titanium oxide);
  calcium carbonate;
  magnesium carbonate or magnesium hydrocarbonate;
  microcrystalline cellulose;
  powders of synthetic polymers, such as polyethylene, polyesters (for example polyethylene isophthalate or terephthalate), and polyamides (for example nylon);
  teflons.

These fillers may represent up to 10% of the total weight of the composition.

The pigments and fillers may be coated with substances such as amino acids, silicones, metal salts or collagen, or any other treatment which allows their surface state to be modified.

The water-soluble polymer(s) contained in the aqueous phase is (are) chosen in particular from the group formed by:
  protein derivatives of animal or plant origin and more particularly keratin derivatives, such as keratin hydrolysates and sulfonic keratins;
  cellulose derivatives, such as hydroxyethylcellulose, hydroxypropylcellulose, methylcellulose, ethylhydroxyethylcellulose and carboxymethylcellulose, as well as quaternized cellulose derivatives;

acrylic polymers, such as polyacrylates and polymethacrylates, as well as acrylic copolymers;

polyvinylpyrrolidones and vinyl copolymers, such as the copolymer of methyl vinyl ether and maleic anhydride or the copolymer of vinyl acetate and crotonic acid;

natural polymers, such as:

gum arabics, guar gum, xanthan derivatives and karaya gum;

alginates and carrageenates;

glycoaminoglycans, hyaluronic acid and derivatives thereof;

deoxyribonucleic acid and salts thereof.

The concentration of water-soluble polymer(s) in the aqueous solution is preferably between about 0.1 and 20% by weight of active materials, and the concentration of aqueous phase relative to the total weight of the composition is preferably between 30 and 70%.

The compositions of the invention may also contain, in addition to the components mentioned above, ingredients conventionally used in make-up compositions for the eye-lashes and chosen especially from emollients, preserving agents, sequestering agents, fragrances, thickeners, oils, silicones, cohesion agents, non-film-forming polymers, basifying or acidifying agents and agents known for their beneficial action on the eye-lashes, such as vitamins or amino acids.

The make-up compositions according to the invention are in the form of a mascara.

Another subject of the present invention is a process for the preparation of a composition for making up the eye-lashes and the eyebrows, as defined above. This process is characterized in that:

in a first step, the components of the fatty phase, the surfactant emulsifying mixture and the optional lipo-soluble additives are mixed together;

in a second step, the optional fillers and/or pigments are added to the mixture obtained;

in a third step, the aqueous phase containing the water-soluble film-forming polymer(s) and the optional water-soluble active additives and/or ingredients are dispersed in the resulting mixture, in the fatty phase.

Another subject of the invention consists of the use of the emulsifying mixtures based on glyceryl acylates, as defined above, as agents for inhibiting microbial growth in cosmetic emulsions.

The Applicant has observed, surprisingly, that the emulsifying mixtures according to the invention had inhibitory properties with respect to the growth of microbial strains responsible for the contamination of cosmetic emulsions, both during their manufacture and during their use. The following strains may be mentioned in particular:

*Escherichia coli*

*Pseudomonas aeruginosa*

*Streptococcus faecalis*

*Candida albicans*

*Aspergillus niger*

The examples which follow serve to illustrate the invention without, however, being limiting in nature.

EXAMPLES

In all the examples which follow, the inhibitory power is determined quantitatively for each cosmetic formula, on a microbial spectrum consisting of collection strains (American Type Culture Collection) representing the potential contaminants of cosmetic products, both during their manufacture and during their use.

| This spectrum is composed of 5 microorganisms: | |
|---|---|
| *Escherichia coli* | (Gram - bacterium) |
| *Pseudomonas aeruginosa* | (Gram - bacterium) |
| *Streptococcus faecalis* | (Gram + bacterium) |
| *Candida albicans* | (Yeast) |
| *Aspergillus niger* | (Mold) |

The inhibitory power is determined according to a method based on the artificial contamination of each cosmetic formula by a defined microbial spectrum, with monitoring of the development of this contamination over time.

Each test composition is subjected beforehand to a control of microbiological cleanliness before being divided into 5 20-gram fractions.

Each of these fractions is then inoculated with one of the microorganisms mentioned above, so as to give a microbial concentration of about $10^6$ microorganisms per gram of product.

The inoculated samples are incubated for 7 days at 22° C., and are then removed in order to evaluate their level of contamination by the conventional Pasteur method.

The difference between the initial contamination level and that after 7 days of microorganisms/product contact allows the inhibitory power of the formula to be measured.

EXAMPLES I and II

|  | I | II (comparative) |
|---|---|---|
| Aminomethylpropanediol stearate (anionic surfactant) |  | 8.6 |
| Aminomethylpropanediol oleate (anionic surfactant) |  | 4.1 |
| Glyceryl stearate (TEGIN M from Goldschmidt) | 3 |  |
| PEG 30 glyceryl stearate (TAGAT S from Goldschmidt) | 7.3 |  |
| Pigments | 5.7 | 5.7 |
| Paraffin (hardness = 15) | 17.5 | 17.5 |
| Carnauba wax (hardness = 1) | 4.4 | 4.4 |
| Water-soluble polymer | 1.2 | 1.2 |
| Butylparaben | 0.1 | 0.1 |
| Methylparaben | 0.2 | 0.2 |
| Disodium EDTA | 0.1 | 0.1 |
| Neutralizing agent | 0.05 | 0.05 |
| Phenylethyl alcohol | 0.5 | 0.5 |
| Water | qs 100 | 100 |

Mascara I is in accordance with the invention. The HLB of the glyceryl stearate/PEG 30 glyceryl stearate emulsifying mixture is 11.8.

Mascara II is a counterpart according to the prior art, containing anionic surfactants.

Mascara I has a better inhibitory power, with respect to microorganisms, than mascara II.

Mascara I is flexible and well tolerated by individuals with very sensitive eyes.

EXAMPLES III and IV

|  | III | IV (comparative) |
|---|---|---|
| Methylglucose sesquistearate (nonionic surfactant) (Glucate SS (Amerchol) | 8.4 | |
| PEG 20 methylglucose sesqui-stearate (nonionic surfactant) (Glucamate SSE) | 2.1 | |
| Glyceryl stearate (TEGIN M from Goldschmidt) | | 2.6 |
| PEG 30 glyceryl stearate (TAGAT S from Goldschmidt) | | 7.9 |
| Beeswax (hardness = 14) | 19.5 | 19.5 |
| Butylparaben | 0.1 | 0.1 |
| Pigment | 5 | 5 |
| Water-soluble polymer | 4.8 | 4.8 |
| Methylparaben | 0.2 | 0.2 |
| Disodium EDTA | 0.1 | 0.1 |
| Neutralizing agent | 0.04 | 0.04 |
| Phenylethyl alcohol | 0.5 | 0.5 |
| Vitamin | 1 | 1 |
| Water | qs 100 | 100 |

Mascara IV is in accordance with the invention. The HLB of the glyceryl stearate/PEG 30 glyceryl stearate emulsifying mixture is 13.5.

Mascara III is a counterpart according to the prior art, containing a nonionic surfactant different from the glyceryl ($C_{10}$–$C_{20}$) acylates of the invention.

Mascara IV has a better inhibitory power, with respect to microorganisms, than mascara III.

Mascara IV is flexible and is well tolerated by individuals with very sensitive eyes.

EXAMPLE V

| | |
|---|---|
| Glyceryl laurate (IMWITOR 312 from Hüls) | 3.5 |
| PEG 30 glyceryl cocoate (VARIONIC LI 63 from Sherex) | 8 |
| Pigment | 6 |
| Beeswax (hardness = 14) | 10 |
| Paraffin (hardness = 15) | 6 |
| Carnauba wax (hardness = 1) | 3 |
| Water-soluble polymers | 3 |
| Methylparaben | 0.2 |
| Propylparaben | 0.1 |
| Disodium EDTA | 0.05 |
| Water | qs 100 |

The HLB of the glyceryl laurate/PEG 30 glyceryl cocoate mixture is 11.9.

The mascara thus obtained has a good inhibitory power and is comfortable to use. Furthermore, it is well tolerated by individuals with very sensitive eyes.

EXAMPLE VI

| | |
|---|---|
| Glyceryl stearate | 1.9 |
| Glyceryl stearate oxyethylenated with 30 mol of ethylene oxide | 5.15 |
| Carnauba wax (hardness = 1) | 12 |
| Paraffin (hardness = 15) | 8 |
| Pigments | 2 |
| Water-soluble polymers | 6.5 |
| Neutralizing agent | qs pH = 7 |
| Preserving agents | qs |
| Water | qs 100 |

When applied to the eyelashes, the mascara retains their flexibility.

We claim:

1. Composition for making up the eyelashes and the eyebrows, comprising a fatty phase based on at least one wax having a melting point between 50° and 100° C. and an aqueous phase based on at least one water-soluble film-forming polymer in solution, comprising:

(a) from 0 to 14% by weight based on the total weight of the composition of at least one wax I having a needle penetration index at 25° C., according to the Reinhold standard, between 1 and 7.5 and from 2 to 40% by weight based on the total weight of the composition of at least one wax II having a needle penetration index at 25° C. and according to the same standard, between 7.5 and 217; the weight ratio of the wax I to the wax II being less than 2; and (b) as emulsifying agent and agent for inhibiting the growth of microorganisms a mixture comprising at least an oxyethylenated glyceryl ($C_{10}$–$C_{20}$) acylate and at least a non-oxyethylenated ($C_{10}$–$C_{20}$) acylate chosen such that the final HLB, in the Griffin sense, of the mixture is between 6 and 15, the oxyethylenated and non-oxyethylenated glyceryl acylates of the emulsifying mixture being glyceryl mono- or polyesters whose degree of saturation ranges from 0 to 3 and for which the number of moles of ethylene oxide range from 0 to 100.

2. Composition according to claim 1, wherein the oxyethylenated glyceryl acylates are glyceryl stearate, glyceryl oleate, glyceryl cocoate, glyceryl laurate or glyceryl isostearate which are polyethoxylated with 30 mol of ethylene oxide or glyceryl trioleate polyethoxylated with 25 mol of ethylene oxide.

3. Composition according to claim 1, wherein the non-oxyethylenated glyceryl acylates are glyceryl stearate or glyceryl laurate.

4. Composition according to claim 1, wherein the emulsifying mixture consists of oxyethylenated glyceryl acylate and of glyceryl stearate.

5. Composition according to claim 1, wherein the emulsifying mixture of glyceryl acylate is within a proportion from 0.5 to 15% by weight based on the total weight of the composition.

6. Composition according to claim 1, wherein the waxes present in the fatty phase are mineral waxes, synthetic waxes or animal waxes having a melting point between 50° and 110° C. and a needle penetration at 25° C., according to the Reinhold standard, between 1 and 7.5 for wax I or between 7.5 and 217 for wax II.

7. Composition according to claim 1, wherein the waxes are candelilla wax, carnauba wax, ouricury wax, sugar cane wax or polyethylene waxes.

8. Composition according to claim 1, wherein the waxes II are beeswax, lanolin waxes, paraffin waxes, cerasin waxes, microcrystalline waxes, ozokerites, spermacetis, polyethylene waxes or hydrogenated plant oils.

9. Composition according to claim 1, wherein the weight ratio of wax I to wax II is less than 1.25.

10. Composition according to claim 1, which contains from 2 to 30% by weight based on the total weight of the composition of wax II.

11. Composition according to claim 1, which is in the form of a wax-in-water emulsion in which the particles of dispersed wax are greater than 1 μm in size.

12. Composition according to claim 1, wherein the weight ratio of the emulsifying mixture of glyceryl acylates relative to the wax is between 0.1 and 0.6.

13. Composition according to claim 1, which additionally contains colored or noncolored fillers.

14. Composition according to claim 1, wherein the concentration of water-soluble film-forming polymer in the aqueous solution is between about 0.1 and 20% by weight of active material, and the concentration of aqueous phase is between 30 and 70% by weight based on the total weight of the composition.

15. Composition according to claim 1, which also contains emollients, preserving agents, sequestering agents, fragrances, thickeners, oils, silicones, cohesion agents, non-film-forming polymers, basifying or acidifying agents, vitamins or amino acids, or another standard active agent or additive used in make-up compositions for eyelashes.

16. A process of using which comprises at least one oxy ethylenated glyceryl ($C_{10}$–$C_{20}$) acylate and at least a second oxyethylenated glyceryl ($C_{10}$–$C_{20}$) acylate or a non-oxyethylenated acylate chosen such that the final HLB, in the Griffin sense, of the said mixture is between 6 and 15, as an agent for inhibiting the growth of microorganisms in cosmetic emulsions.

17. Composition according to claim 1, wherein the water-soluble film-forming polymer contained in the aqueous phase is a protein of animal or plant origin;

a cellulose;

acrylic polymers;

polyvinylpyrrolidones or water-soluble vinyl copolymers;

gum arabics, guar gum, a xanthan, karaya gum, alginates, carrageenates, glycoaminoglycans, an hyaluronic acid, or deoxyribonucleic acid or salts thereof.

* * * * *